United States Patent [19]
Bekkering et al.

[11] 4,291,695
[45] Sep. 29, 1981

[54] DISPOSABLE INJECTION SYRINGE

[75] Inventors: Hendrik M. Bekkering, Olst; Ernst M. Schmidt, Eindhoven, both of Netherlands

[73] Assignee: Duphar International Research B.V., Weesp, Netherlands

[21] Appl. No.: 146,152

[22] Filed: May 2, 1980

Related U.S. Application Data

[63] Continuation of Ser. No. 929,167, Jul. 28, 1978, abandoned, which is a continuation of Ser. No. 783,943, Apr. 1, 1977, abandoned.

[51] Int. Cl.³ .............................................. A61M 5/00
[52] U.S. Cl. ............................... 128/218 NV; 128/220
[58] Field of Search ............ 128/215, 218 P, 218 NV, 128/218 M, 220, 221, 234

[56] References Cited

U.S. PATENT DOCUMENTS

| | | | |
|---|---|---|---|
| 1,987,146 | 1/1935 | Hein | 128/218 P |
| 2,842,126 | 7/1958 | Brown | 128/218 NV |
| 2,894,509 | 7/1959 | Bednarz | 128/218 NV |
| 3,084,688 | 4/1963 | McConnaughey | 128/218 NV |
| 3,091,240 | 5/1963 | McConnaughey | 128/218 NV |
| 3,380,449 | 4/1968 | Sarnoff | 128/218 NV |
| 3,391,695 | 7/1968 | Sarnoff | 128/218 NV |
| 3,424,155 | 1/1969 | Sarnoff | 128/218 NV |
| 3,710,794 | 1/1973 | Shields | 128/218 NV |
| 3,756,390 | 9/1973 | Abbey et al. | 128/218 M |
| 3,921,633 | 11/1975 | Tischlinger | 128/215 |
| 3,987,940 | 10/1976 | Tischlinger | 128/218 R X |

FOREIGN PATENT DOCUMENTS

| | | | |
|---|---|---|---|
| 3370 | 2/1902 | Fed. Rep. of Germany | 128/218 P |
| 2258371 | 6/1974 | Fed. Rep. of Germany | 128/218 R |
| 328570 | 5/1903 | France | 128/218 NV |

*Primary Examiner*—John D. Yasko
*Attorney, Agent, or Firm*—Witherspoon & Hargest

[57] ABSTRACT

A disposable injection syringe having a very small volume of unusable injection liquid. The liquid container has a constant diameter over its entire length so that the plunger can move at least all the way to the needle connection end of the container.

5 Claims, 8 Drawing Figures

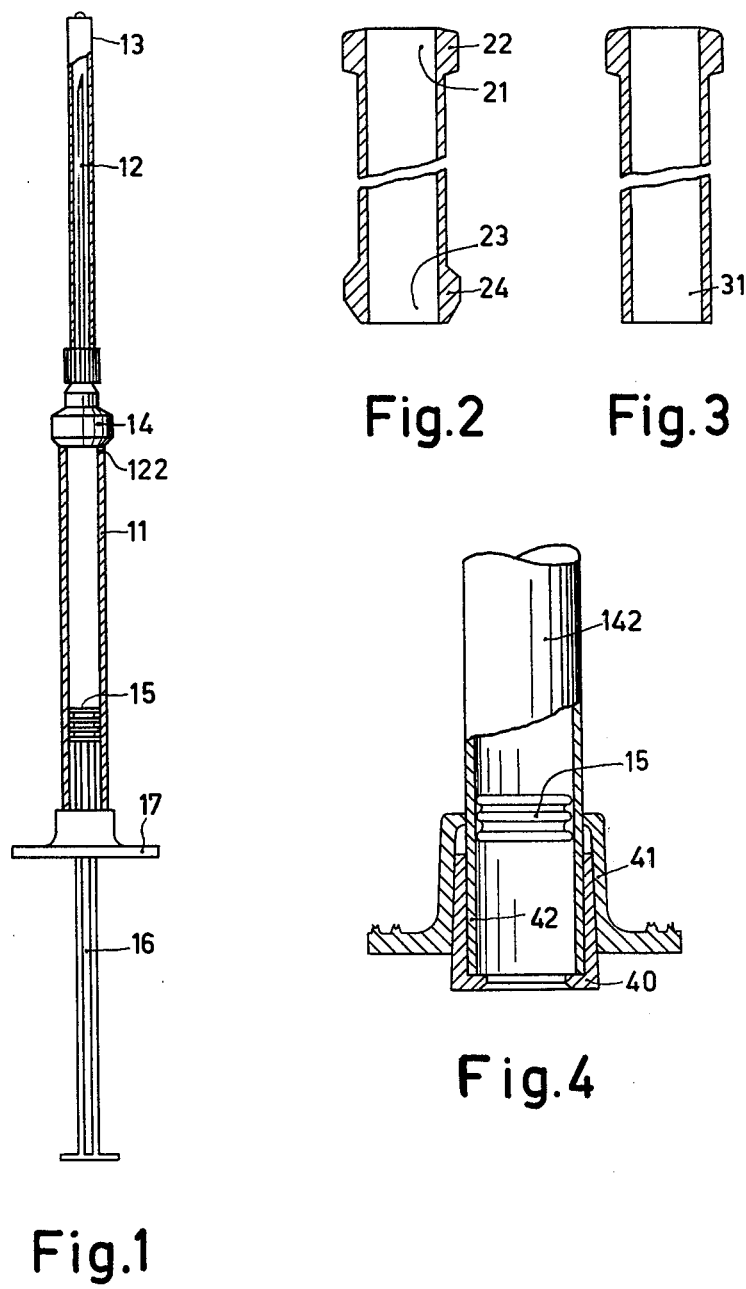

DISPOSABLE INJECTION SYRINGE

This is a continuation of application Ser. No. 929,167 filed July 28, 1978 now abandoned which in turn is a continuation of Ser. No. 783,943, filed Apr. 1, 1977 now abandoned.

BACKGROUND OF THE INVENTION

1. Field of the Invention

The invention relates to a disposable injection syringe and in particular to an injection syringe having a cylindrical liquid container with needle connection means at one container end and a plunger in the container for movement by a plunger rod so as to eject material to be injected.

In the design of such syringes reduction of the amount of liquid remaining is desirable. The development of new medicines involves steadily increasing costs for research in an industry which is heavily research-based, particularly because of the requirements imposed on new medicines by national authorities and advances in medical science, so that the costs of medicines are rising continually. Further, in a continuing effort to minimize the quantity of material being administered to patients, there is a trend to administer relatively smaller quantities of injection liquid than previously, and therefore injection syringes with smaller capacities are desirable. Another disadvantage of a large quantity of unusable injection liquid is that is may needlessly impair the environment when a used syringe is destroyed.

2. Description of the Prior Art

Injection syringes, both disposable and reusable, have been used for many years for injection of medicines into patients. All of these syringes have had the disadvantage that not all the liquid contained within the syringe can be administered. In part, this occurs because a quantity of injection liquid remains in the needle; however, at least part of the disadvantage arises because the plunger cannot be moved entirely to the end of the liquid-containing portion of the syringe, that is, to the beginning of the needle. Thus there is often a quantity of injection liquid left between the plunger piston and the beginning of the needle.

This problem is particularly noticeable in disposable syringes which are pre-filled with medicine by the manufacturer. To permit long storage times of such pre-filled syringes without excessive degradation of the medicine, in most cases it is necessary to protect the injection liquid from deterioration which would result from extended contact with the material from which the needle or needle connection means are made, these devices usually being made from a metal or a synthetic resin. Therefore a sealing member is often provided at the needle end of the liquid container, the sealing member being manufactured from a rubber material of a pharmaceutical quality, or from a corresponding chemically inert material. The plunger is made from materials which are similarly selected. As a result, during storage the injection liquid contacts only the materials from which the liquid container, the plunger and the sealing member are made.

Disposable syringes of the previously known types have an obstruction or an inwardly extending flange which is formed by a portion of the liquid container itself at the needle connection end. This flange can serve both for attachment of the needle hub, and as a stop, limiting the motion of the plunger, and thereby resulting in the formation of a central region within the constriction, wherein unused injectable liquid collects. Normal injection syringes of the types described above, depending on their capacity, generally contain a volume between 0.1 and 0.3 ml of unusable injection liquid. Reduction of this unusable quantity to a minimum is desirable, particularly where expensive medicines are involved or injection syringes of small capacity are to be used.

SUMMARY OF THE INVENTION

An object of the invention is to minimize the quantity of unusable medication which is wasted whenever an injection is to be made.

A further object of the invention is to provide a disposable syringe having a minimum quantity of liquid in the space remaining between the plunger and the injection needle.

In accordance with the invention, a syringe is provided in which the liquid container is manufactured so as to have its inside diameter constant throughout the entire length of the container.

This solution to the problem, which may at first seem almost self-evident, has in practice not proved possible for a disposable injection syringe which has a simple structure and inexpensive manufacturing cost. For example, British patent specification No. 704,259 describes a re-usable syringe which can be easily and rapidly dis-assembled but requires an expensive and complicated construction with several ground parts, screwed connections and the like. Of course, this could not reasonably be used or described as a disposable syringe.

In a preferred embodiment of the invention a pre-filled syringe includes a flexible sealing member between the needle or needle connection means and the injection agent, and extending a short distance into the liquid container. Because of the construction of the container according to the invention, and the flexibility of the sealing member, it is possible to move the plunger even beyond the end of the actual liquid container, thus dispensing almost all of the remaining liquid behind the sealing member. By use of this construction, the volume of remaining liquid can be reduced to less than 0.05 ml, a saving of 50–80% compared with previously known syringes. This construction is especially advantageous when the sealing member is of the type used in the "Cartrix" system, having a thin elastic diaphragm which can be ruptured by pressure, such as the syringe described in U.K. patent Nos. 1,203,098 and/or 1,210,676.

BRIEF DESCRIPTION OF THE DRAWING

The invention is described in detail hereinafter in connection with the drawing in which:

FIG. 1 is a side view, partially in section, of a complete injection syringe according to the invention, FIG. 2 is a cross-sectional view of a liquid container having a thickened outer portion at each end, FIG. 3 is a cross-sectional view of another embodiment of a liquid container having a thickened portion at the needle connection end only.

FIG. 4 is a side view, partially in section, of the holder end of a syringe having a liquid container according to FIG. 3.

DESCRIPTION OF THE PREFERRED EMBODIMENTS

Figure 5:
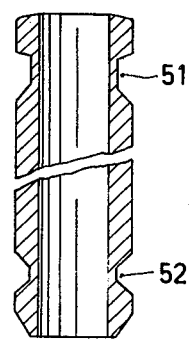
FIG. 5 is a cross-sectional view of still another embodiment of a container according to the invention having notches at each end for connection of the needle and a finger grip.

In FIG. 1 a complete injection syringe according to the invention is shown. A circular cylindrical liquid container 11 communicates with an injection needle 12, prior to use the needle being covered by a protection cap 13. A needle connection means 14, for example a formed metal sleeve crimped at one end around the exterior of the needle, is fitted snugly over a needle connection end 122 of the container 11. Fitted liquid-tight in the container 11 is a plunger 15 attached to a plunger rod 16, the rod passing through a finger-grip 17 attached at the end of the container 11 remote from the needle connection means 14.

FIG. 2 shows in cross-section a first embodiment of a liquid container usable in the syringe shown in FIG. 1. The needle connection end 21 of the container has a thickened portion 22 protruding outward in comparison with the main portion of the container, so that a needle or needle connection means can be fastened thereabout. At the opposite end 23 a similar thickened portion 24 provides an external circumferential ridge for attachment of a finger-grip. It will of course be clear that neither the thickened portion 22 nor the portion 24 need by cylindrical in their exterior surfaces, although this is a preferred embodiment leading to simplicity in manufacture. The important feature is that the entire length of the inner surface be circular cylindrical; that is, of constant diameter.

FIG. 3 shows similarly in cross-section another embodiment of a liquid container usable with the syringe of FIG. 1. This differs from the FIG. 2 embodiment in that the finger-grip connection end 31 does not have a thickened portion. Such a container is readily used with a holding means such as that described in the U.S. Pat. No. 3,921,633. Such a finger-grip holding means is shown in FIG. 4, in which a tensioning ring or collet 40 is pressed tightly inward by a tensioning sleeve 41, the ring 40 being held against an end portion 42 of a liquid container 142. The plunger rod can be attached to the plunger with means known per se; e.g., a screw-thread connection or a snap connection.

Figure 6:
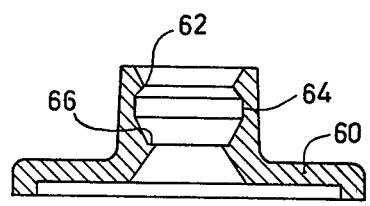
FIG. 6 is a sectional view of a finger grip suitable for use with the container of FIG. 5.

FIG. 5 shows in cross-section still another embodiment of a cylindrical liquid container according to the invention, having the outside diameter substantially constant throughout its length. To attach the needle, a notch 51 is formed in the outer surface of the container at the needle attachment end, and a notch 52 is formed in the outer surface at the finger-grip connection end. A finger grip 60 suitable for use with either the container of FIG. 2 or 5 is shown in FIG. 6, the grip having an inward circumferential ridge 62 adapted for engaging in the notch 52 of the FIG. 5 container. For use with the container of FIG. 2, the projection 24 shown in FIG. 2 fits in the internal circumferential depression 64 between the ridge 62 and an end stop 66 projecting inwardly.

Figure 7:
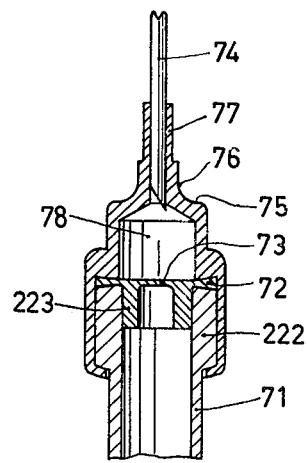
FIG. 7 is a cross-sectional view of the needle connection portion of a syringe having a tearable diaphragm as a sealing member, using the container of FIGS. 2 or 3.

FIG. 7 shows the preferred embodiment of a needle connection end and needle connection used with the invention. A liquid container 71 similar to that shown in FIG. 2 or FIG. 3 has a thickened end portion 222. A sealing member 72 is held against an end face of the portion 222, the center of the sealing member having an elastic diaphragm 73 so proportioned that it can be ruptured by pressure from the interior of the container. Surrounding the diaphragm 73 is a tubular portion 223 extending a short distance inside the container 71. At the other end of the connection means 14 is a needle 74 held firmly in a needle hub 75 by crimping or shrinking. At an upper end 76 of the hub provision is made for mounting of a needle protection cap such as the cap 13.

Because of the flexibility of the sealing member 72, upon movement of a plunger 15 through the container 71 into contact with the extending portion 222, the plunger deflects the extending portion 223 and the diaphragm 73 into a space 78 in the means 14 so as to permit the plunger to pass to or beyond the end of the container 71 so as to expel a maximum proportion of injectable liquid which was contained in the space 78.

Figure 8:
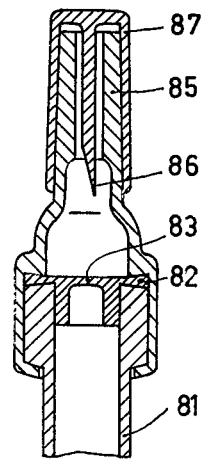
FIG. 8 is a cross-sectional view of another embodiment of a syringe according to the invention having a Luer cone for a needle connection means.

Still another embodiment of a connection means is shown in FIG. 8, the container 81, sealing member 82 and diaphragm 83 being otherwise similar to those shown in FIG. 7 and having related reference numerals. The end of the attachment means remote from the liquid container has a Luer cone 85, of the well-known type to which a needle can be connected immediately prior to use of the syringe. Before attaching the needle, the syringe is activated by causing the elastic diaphragm 83 to tear against a sharp tip 86 provided on a cap 87 which is used to seal the Luer cone before use, for example as taught in Dutch patent application No. 72.07394.

By way of example, a syringe constructed according to the preferred embodiment of FIG. 1 and having an inside diameter of the liquid container of approximately 4.7 mm, was found to have a useless remaining liquid which was less than 0.05 ml. Such a syringe, when constructed with a capacity of 0.5 ml, may find application in large quantities, for administering medicine to control thrombosis. The syringe according to the invention thus may have an unused volume of less than 10% of the original volume, in contrast with a waste of 20 to 60% when the prior known syringe types are used.

It will be clear to those skilled in the art that many other modifications of the embodiment shown and described are possible while incorporating the spirit of the invention. For example, the entire liquid container may be placed in a holder suitable for that purpose, such as that shown in U.S. Pat. No. 3,976,069. Whether of the design shown therein, or designs shown in the various figures of the accompanying drawing, the various parts of the syringe may be manufactured from any material which is suitable for the intended purpose and medicament. Preferably, however, the liquid container consists of glass. The plunger and the sealing member, when used, preferably consists of a pharmaceutical grade of rubber.

What is claimed is

1. A disposable syringe comprising:
   a cylindrical body having a constant internal diameter throughout its length, connecting means on the outer portion of the cylindrical body adjacent the forward end thereof;

a needle hub assembly affixed to the forward end of the cylindrical body, said needle hub assembly including a hub portion having locking means coacting with the connecting means on the forward end of the cylindrical body to retain the needle hub assembly on the forward end of the cylindrical body, said hub portion including a needle mounting portion extending forwardly from the forward end of the cylindrical body, the inner diameter of the needle mounting portion adjacent the forward end opening of the cylindrical body having a diameter at least as large as that of the inner diameter of the cylindrical body to form a hub chamber, said needle mounting portion having a forward section adapted to receive an injection needle;

a rupturable sealing member closing off the forward end of the cylindrical body; plunger means sealingly and slidably positioned in the cylindrical body adjacent the rearward end thereof to form a medicament chamber between the plunger means and the sealing member; and a finger grip affixed to the rearward end of the cylindrical body, the sealing member being sufficiently flexible whereby the pressure developed by forward movement of the plunger means will rupture said sealing member and commence the flow of the medicament into the hub chamber and out of the needle and wherein continued forward movement of the plunger means will result in travel thereof into the hub chamber to fully inject the major portion of the medicament carried by the medicament chamber.

2. The invention as set forth in claim 1 and wherein the rupturable sealing member comprises:

a relatively thin center portion surrounded by a rearwardly extending annular portion whose outer surface snugly engages the inner wall of the cylindrical body and a flange portion extending radially outward from the annular portion to fit over the forward end of the cylindrical body whereby the plunger means near the end of its travel will engage the rearward face of the annular portion so that upon continued travel the plunger means will force the annular portion into the hub chamber to provide for maximum injection of medicament.

3. A disposable syringe comprising:

a cylindrical body having a constant internal diameter throughout its length, a peripheral notch formed in the outer portion of the cylindrical body adjacent the forward end thereof, a second peripheral notch formed in the outer portion of the cylindrical body adjacent the rearward end thereof to provide an annular flange equidistantly spaced from each end of the cylindrical body;

a needle hub assembly affixed to the forward end of the cylindrical body, said needle hub assembly including a hub portion having a locking flange fitting down into the peripheral notch in the forward end of the cylindrical body and over the annular flange to retain the needle hub assembly on the forward end of the cylindrical body, said hub portion including a needle mounting portion extending forwardly from the forward end of the cylindrical body, the inner diameter of the needle mounting portion adjacent the forward end opening of the cylindrical body having a diameter at least as large as that of the inner diameter of the cylindrical body to form a hub chamber, said needle mounting portion having a forward section adapted to receive an injection needle;

a resilient and rupturable sealing member closing off the forward end of the cylindrical body;

plunger means sealingly and slidably positioned in the cylindrical body adjacent the rearward end thereof to form a medicament chamber between the plunger means and the sealing member; and a finger grip affixed to the rearward end of the cylindrical body, said finger grip including an inwardly projecting circumferential locking bead fitting into the second peripheral notch in the rearward end of the cylindrical body and over the annular flange to firmly retain the finger grip on said body, said finger grip having an inwardly extending flange which engages the rearward end of the cylindrical body and extends slightly into the inner diameter of the cylindrical body to retain the plunger means therein; the sealing member being sufficiently flexible whereby the pressure developed by forward movement of the plunger means will rupture the sealing means and commence the flow of the medicament into the hub chamber and out the needle and wherein continued forward movement of the plunger means will result in travel into the hub chamber to fully inject the major portion of the medicament carried by the medicament chamber.

4. The invention as set forth in claim 3 and wherein the rupturable sealing member comprises:

a relatively thin center portion surrounded by a rearwardly extending annular portion whose outer surface snugly engages the inner wall of the cylindrical body and a flange portion extending radially outward from the annular portion to fit over the forward end of the cylindrical body whereby the plunger means near the end of the travel will engage the rearward face of the annular portion so that upon continued travel the flunger means will force the annular portion into the hub chamber to provide for maximum injection of medicament.

5. A disposable syringe comprising:

a cylindrical body having a constant internal diameter throughout its length, a peripheral notch formed in the outer portion of the cylindrical body adjacent the forward end thereof to provide an annular flange equidistantly spaced from said end of the cylindrical body;

a needle hub assembly affixed to the forward end of the cylindrical body, said needle hub assembly including a hub portion having a locking flange fitting down into the peripheral notch in the forward end of the cylindrical body and over the annular flange to retain the needle hub assembly on the forward end of the cylindrical body, said hub portion including a needle mounting portion extending forwardly from the forward end of the cylindrical body, the inner diameter of the needle mounting portion adjacent the forward end opening of the cylindrical body having a diameter at least as large as that of the inner diameter of the cylindrical body to form a hub chamber, said needle mounting portion having a forward section adapted to receive an injection needle;

a rupturable sealing member closing off the forward end of the cylindrical body;

plunger means sealingly and slidably positioned in the cylindrical body adjacent the rearward end thereof to form a medicament chamber between the plunger means and the sealing member; and a finger grip affixed to the rearward end of the cylindrical body, said finger grip having an inwardly extending flange which engages the rearward end of the cylindrical body and extends slightly into the inner diameter of the cylindrical body to retain the plunger means therein, the sealing member being sufficiently flexible whereby the pressure developed by forward movement of the plunger means will rupture the sealing member and commence the flow of the medicament into the hub chamber and out of the needle and wherein continued forward movement of the plunger means will result in travel thereof into the hub chamber to fully inject the major portion of the medicament carried by the medicament chamber.

* * * * *